United States Patent [19]
Silén et al.

[11] Patent Number: 5,728,537
[45] Date of Patent: Mar. 17, 1998

[54] METHODS OF PRODUCING ANTIBODIES AGAINST CYTOKERATON FRAGMENTS AND TEST KITS CONTAINING SUCH FRAGMENTS

[75] Inventors: Åke Silén, Vällingby; Bo Wiklund, Upplands Väsby, both of Sweden

[73] Assignee: AB IDL Immunodeveloplab, Sollentuna, Sweden

[21] Appl. No.: 30,100

[22] PCT Filed: Sep. 24, 1991

[86] PCT No.: PCT/SE91/00638

§ 371 Date: Mar. 23, 1993

§ 102(e) Date: Mar. 23, 1993

[87] PCT Pub. No.: WO92/05197

PCT Pub. Date: Apr. 2, 1992

[30] Foreign Application Priority Data

Sep. 24, 1990 [SE] Sweden ................... 9003025

[51] Int. Cl.$^6$ .................. G01N 33/574; C12P 21/08
[52] U.S. Cl. .................. 435/7.23; 435/7.21; 435/70.2; 435/70.21; 435/172.2; 435/240.27; 436/64
[58] Field of Search .................. 435/7.2, 7.21, 435/7.23, 240.26, 240.27, 70.2, 70.21, 172.2; 436/64; 530/357, 388.8, 388.85, 389.7, 412

[56] References Cited

U.S. PATENT DOCUMENTS

| | | | |
|---|---|---|---|
| 4,722,895 | 2/1988 | Yuspa et al. | 435/68 |
| 4,727,021 | 2/1988 | Cote et al. | 435/7.21 |
| 4,775,620 | 10/1988 | Cardiff et al. | 435/7.21 |

FOREIGN PATENT DOCUMENTS

| | | |
|---|---|---|
| 0267355 | 5/1988 | European Pat. Off. . |
| 0267356 | 5/1988 | European Pat. Off. . |
| 0337057 | 10/1989 | European Pat. Off. . |

OTHER PUBLICATIONS

Harlow et al., *Antibodies, A Laboratory Manual*, Cold Spring Harbor Laboratory, (1988), pp. 59–61.

Mellerick et al., Oncogene, vol. 5 (Jul. 1990) pp. 1007–1017, "On the nature of serological tissue polypeptide antigen (TPA); monoclonal keratin 8, 18, and 19 antibodies react differently with TPA prepared from human cultured carcinoma cells and TPA in human serum".

Moll et al., Cell, vol. 31, (Nov. 1982), pp. 11–24, "The Catalog of Human Cytokeratins: Patterns of Expression in Normal Epithelia, Tumors and Cultured Cells".

Basta, et al. (1988) British Journal of Urology, 61:116–121.

Herrmann et al. (1985) Abstract, File 155, Access No. 05645631.

Settle et al. (1985) Experimental Cell Research, 157:293–306.

Osborn et al. (1986) Laboratory Investigation 55:497–504.

Debus et al. (1982) The Embo Journal, 12:1641–1647.

Schaafsma et al. (1990) American Journal of Pathology 136:329–343.

Chemical Abstracts vol. 106, No. 25 (1987), Abstract No:210597h.

*Primary Examiner*—Lora M. Green
*Attorney, Agent, or Firm*—Birch, Stewart, Kolasch & Birch, LLP

[57] ABSTRACT

Provided is a method for reproducible production of cytokeratin antigen immunogen. Cytokeratins from whole carcinoma cells are purified by preparative SDS-PAGE. Bands corresponding to cytokeratins 8, 18, and 19 are eluted from the gel, and these cytokeratins are digested to produce fragments in the size range of 10–50 Kd. The invention also relates to use of these fragments as immunogens for the production of antibodies. Furthermore, the invention relates to an immunochemical test kit to detect cancer of epithelial origin in body fluids. The kit comprises cytokeratin fragments produced by the method of the invention and antibodies to these fragments.

11 Claims, 11 Drawing Sheets

METHODS OF PRODUCING ANTIBODIES AGAINST CYTOKERATON FRAGMENTS AND TEST KITS CONTAINING SUCH FRAGMENTS

BACKGROUND OF THE INVENTION

1. Field of the Invention

The present invention relates to tumour markers, more specifically cytokeratins, for cancer cells of epithelial origin. According to the invention a method for reproducible production of cytokeratin antigen/immunogen is provided.

There is a large need to be able to detect and diagnose cancer in an early stage before the patient has developed an inoperable tumour or metastases. Furthermore, it is desirable to be able to localize the tumour for localized treatment or prior to surgery.

An example of localized cancer treatment is where the tumour is killed with antibodies coupled to, for example, cytotoxin or radioactive isotopes according to known methods. These substances targeted against the tumour provide increased killing of tumour cells or an increase of the concentration of cytotoxin in the tumour and thereby decrease the side effects of the conventional cytostatic treatment.

From immunohistological and immunocytological tests it is known that certain carcinomas, i.e., tumour tissue of epithelial origin, contain tumour markers in the form of cytokeratins of different kinds. There are 19 different characterized cytokeratins, all being built of proteins. These cytokeratins form so called intermediate filament in the cells. The cytokeratin pair 8 and 18 are very frequent in simple epithelia.

The present invention is based on the discovery that the insoluble intracellular cytokeratins are released and fragmented in tumour tissues, whereby a large fraction of the cytokeratins becomes soluble. The soluble cytokeratin fragments leak out to surrounding body fluids, such as blood, urine, ascites and pleura.

2. Description of Related Art

In U.S. Pat. No. 4,774,620 cytokeratin fragments released in tissue culture medium of MCF-7 carcinoma cells are used to produce monoclonal antibodies. This method is not reproducible and is very unspecific since the actual tumour marker is not exactly known. Because unspecific cell material also is used as reference in tests, the latter become unreliable as regards quantification and specificity.

In EP A1 337 057 cytokeratins are chromatographically purified and enzyme digested to obtain "the alpha helical center portions thereof" which in turn are chromatographically purified and used as antigen in immunological tests and for production of monoclonal antibodies, respectively. Here the antigens/immunogen is obtained in a reproducible way. These known methods are sufficient for detecting cytokeratin fragments in body fluids and for characterizing to which cell category/type a tumour belongs to. However, the monoclonal antibodies obtained according to EP A1 337 057 require an initial solubilization of the sample to be tested.

SUMMARY OF THE INVENTION

Thus, there still exists a need to be able to detect and localize carcinomas in vivo and treat cancer patients with monoclonal antibody therapy. Also, there is a need of more simple and sensitive tests than those of the prior art for determining whether a tumour is progressive or not and following up monoclonal antibody therapy to evaluate the treatment. The present invention fulfils the above needs.

The cytokeratin fragments produced according to the present invention cause a stronger immune response of an animal injected therewith, and therefore higher reactivity and specificity of the antibodies, than those of the prior art. The present invention also gives a more appropriate reaction with several different sizes of cytokeratin fragments, although with retained specificity.

Below the invention will be described in a non limiting way. The abbreviations used are given at the end of the description.

DETAILED DESCRIPTION OF THE INVENTION

Figure 1:
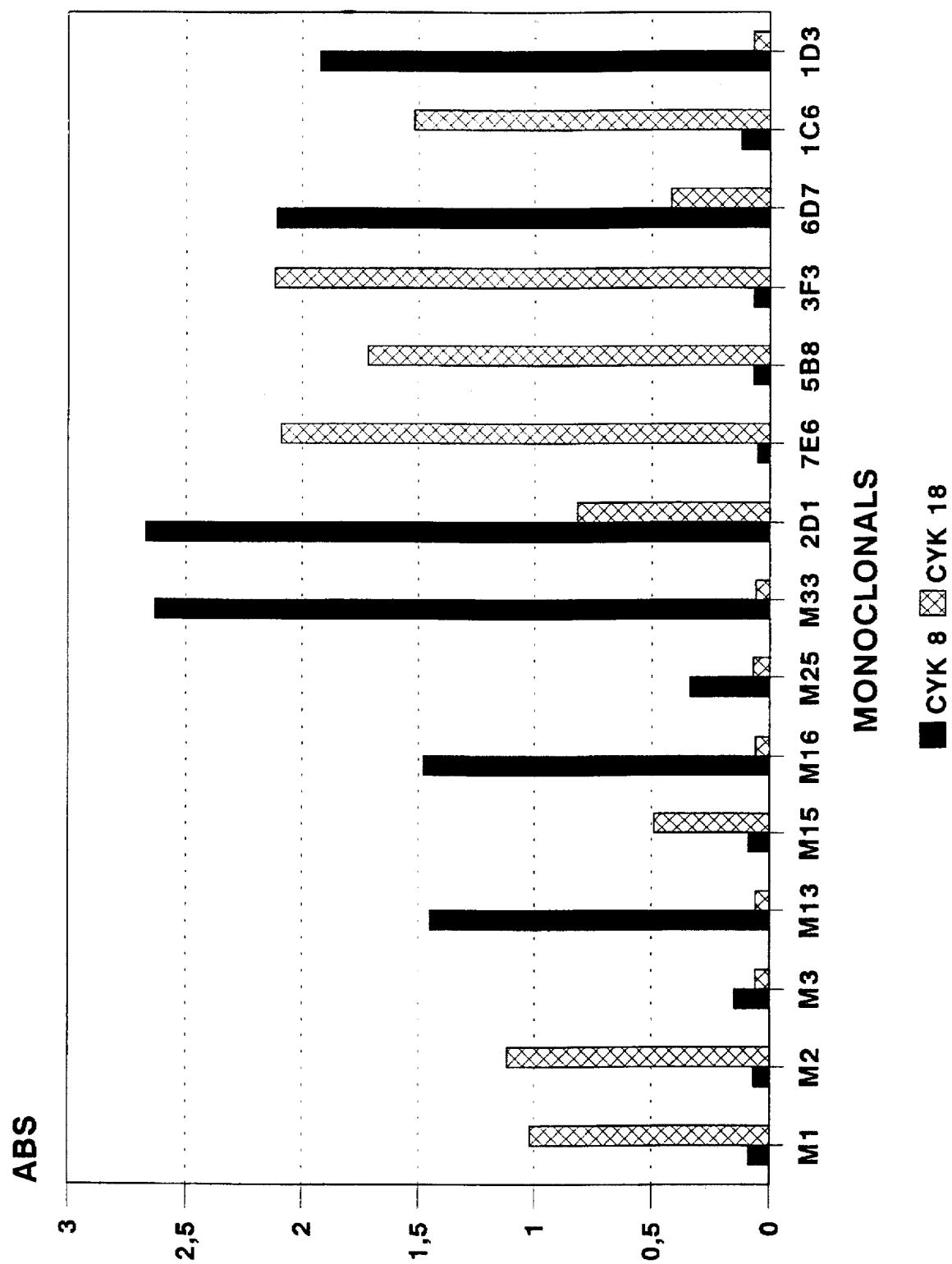
FIG. 1 is a bar graph showing the specificity and reactivity of 15 different monoclonal antibodies of the present invention in ELISA for cytokeratin 8 (left bar), and 18 (right bar).

Production of the Cytokeratins (CYK) 8, 18 and 19

Cytoskeleton of the tumour cell line MCF-7, ATCC no. HTB 22, a human breast cancer adenocarcinoma cell line from pleura fluid, was prepared according to known methods, i.e., Geisler N., Weber K., Eur. J. Biochem. 111, 425–433, 1980. Other tumour cell lines of epithelial origin can also be used, for example DU 145 (ATCC no. HTB 81), HeLa (ATCC no. CCL 2) etc.

This material was purified by preparative SDS-PAGE, wherein the molecular weights in relation to molecular weight references showed about 53, 45 and 41 Kd for the cytokeratins 8, 18 and 19, respectively. This pattern has previously been shown for these cytokeratins. (Moll R., Franke W. W., Schiller D. L. et al. Cell 31, 11–24, 1982).

The bands corresponding to the cytokeratins 8, 18 and 19 were cut out from the gel and extracted with 0.1% SDS, PBS pH 7.5 according to conventional technique. A sample thereof was run on an analytical SDS-PAGE to verify the purity; the result was single bands for each of the cytokeratins 8, 18 and 19 having the same mobility as the three bands in the initial material. This verifies that the cytokeratins 8, 18 and 19 have been purified and maintained their size.

Fragmentation of the Purified Cytokeratins 8, 18 and 19

According to the present invention, the fragmentation of cytokeratins can be made either enzymatically or chemically, with for example chymotrypsin, V8 protease, pepsin, TPCK trypsine, BrCN, partial hydrolysis, BNPS Saktole, etc., provided that a reproducible cleavage pattern is obtained with molecular weights between about 10 to about 50 Kd of the cytokeratin fragments. Because of the purification method according to the present invention, the fragments do not aggregate, but are kept in a monomeric form. This is very important when the fragments are to be used for antibody production as aggregates tend to cause masking of the epitopes.

In a preferred embodiment of the invention the purified cytokeratins 8, 18 and 19 are fragmented, each separately, in a controllable manner by chymotrypsin, with a weight ratio enzyme:cytokeratin of about 1:50–1:1000, the preferred weight ratios being 1:400 (CYK 8), 1:100 (CYK 18) and 1:75 (CYK 19). The activity of the enzyme is 40–60 units per mg of protein. The concentration of cytokeratins is 0.2 mg/ml. A cytokeratin solution and an enzyme solution are each preincubated separately for 5 min. in a 37° C. waterbath. Thereafter the enzyme solution is added to the cytokeratin solution and the mixture is incubated for an additional 5 min. in a 37° C. waterbath. The digestion is stopped by adding a small volume of 20% SDS solution and a final incubation for 5 min. in a 95° C. waterbath. The final SDS concentration will be 2%.

Following the digestion an optional purification of the fragments is performed. The fragments are purified on a preparative SDS-PAGE and after the electrophoresis a thin gel strip is cut out from the gel and stained for a short time in Coomassie Blue solution. Following destaining the position of the different fragments are determined and these parts of the remaining gel is cut out from the gel and extracted with 0.1% SDS in phosphate buffer, pH 7.5. A rerun in an analytical SDS-PAGE verifies the purity.

Fragments having sizes in the range 10–50 Kd are eluted as above. Also, this optional SDS-PAGE of the fragments allows selection of specific fragments. A possible application of this is to immunize mammals with only one or a few cytokeratin fragments. The special fragment(s) giving especially-reactive antibodies from an animal injected therewith are sequenced. On the basis of this sequence, a synthetic nucleotide sequence is made being inserted into a vector, e.g., a plasmid, and cloned in e.g., a bacterium for large scale production of the desired fragment.

Production of Monoclonal Antibodies Directed against Fragmented Cytokeratins 8, 18 and 19

Cytokeratin fragments in the size range of 10–50 Kd from CYK 8, 18 and 19, each purified separately, were dialyzed against 0.1% SDS in PB and thereafter they were immunized in Balb/c mice according to standard procedures, 10 µg fragments per mouse in FCA (s.c.), 10 µg per mouse in FIA, followed by 1 µg per mouse in FIA twice, all with an interval of one week. The mice were boostered 3 times with one day in between before injection.

72 hours after the last boost, lymphocytes from the spleen of the mice were collected and fused with Sp2/0 myeloma cells in the relation 1:1. Of course, it is possible to use other mouse species and myeloma cells. The hybridoma cells were allowed to grow and were cloned according to known methods twice with a dilution technique. One cell per well was established by checking the microtiterplates under a microscope. The hybridoma cells were allowed to grow, stabilized and established. A total of 15 clones was established producing monoclonal antibodies having the specificity and reactivity described below.

Test of the Specificty and Reactivity of the Obtained Monoclonals

A. ELISA TEST WITH WHOLE CYTOKERATINS 8, 18 AND 19 AS ANTIGEN

When testing the obtained monoclonal antibodies in ELISA, against purified cytokeratin 8, 18 and 19 separately coupled to microtiter plates by adsorption at pH 9.0, it appears that some monoclonals have specificty against one, two or all three cytokeratins, but with different reactivity.

Figure 2:
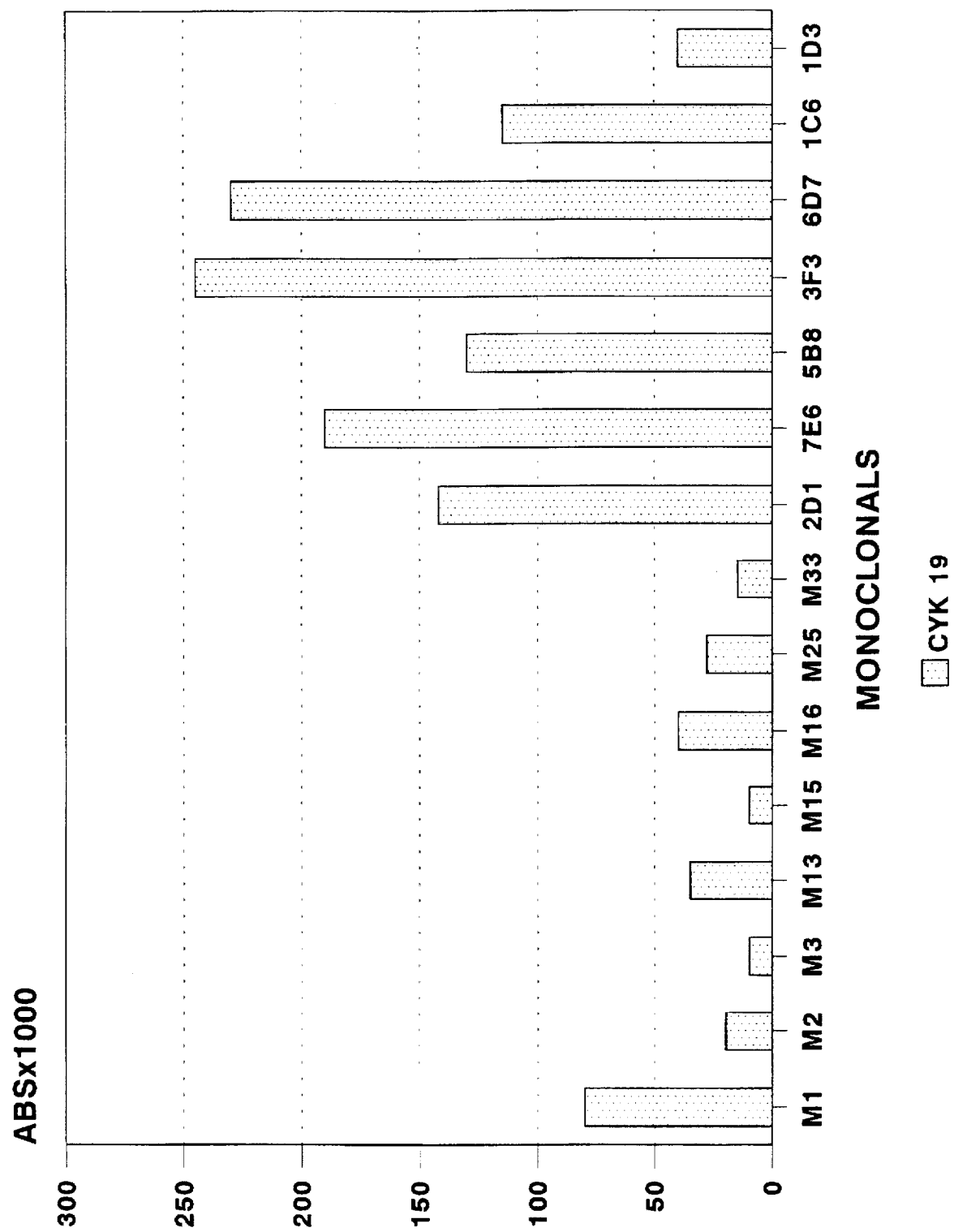
FIG. 2 is a bar graph showing the specificity and reactivity of 15 different monoclonal antibodies of the present invention against cytokeratin 19 in ELISA, as in FIG. 1. Five clones are regarded as being reactive with cytokeratin 19.

The result of testing the 15 above obtained clones at a concentration 10 ng/ml of the monoclonals, is shown in FIGS. 1 and 2, where the reactivity is expressed as absorbance units (490 nm) on the y-axis. FIG. 1 is a bar chart showing the specificity and reactivity of the 15 different monoclonal antibodies in ELISA for cytokeratin 8 (left bar), and 18 (right bar).

The concentration of the antigens; i.e., cytokeratin 8, 18, and 19, coupled on the plates was each 0.3 µg/ml. The primary incubation with the monoclonals was only for 1 hour at RT. Therefore, only the monoclonals with the highest reactivity were selected. The secondary antibodies were anti mouse IgG antibodies (i.e., Dakopatts Code P260) coupled to HRP in a dilution of 1:1000, incubated for another 2 hours RT, and after addition of the substrate o-phenylendiamine, the absorbance at 490 nm was read according to conventional ELISA technique. As appears from FIG. 1, eight clones have the highest reactivity against cytokeratin 8 while the other seven have the highest reactivity against cytokeratin 18.

The bar chart according to FIG. 2 shows the specificity and reactivity of the 15 different monoclonals against cytokeratin 19 in ELISA (as above). Five clones are regarded as being reactive with cytokeratin 19.

As appears from the figures, there is cross reactivity between the different cytokeratins and this is probably due to the large amino acid homologics that are present between cytokeratins 8, 18 and 19. (Leube R. E., Bosch F. X., Romano V. et al, Differentiation 33, 69–85, 1986; Romano V., Hatzfeld M., Magin T. M., et al. Differentiation 30, 244–253, 1986; and Bader B. L., Magin T. M., Hatzfeld M., Franke W. W. EMBO J. 5, 1865–1875, 1986.)

B. WESTERN BLOT WITH FRAGMENTED CYTOKERATIN 8, 18 AND 19 AS ANTIGEN

Western blot of cytokeratin fragments was performed in that the cytokeratins, enzyme digested as above, were run in SDS-PAGE and thereafter were blotted onto nitrocellulose filters according to known methods. In this way it was shown that the monoclonal antibodies identified the majority of the cytokeratin fragments from the respective cytokeratin. Rabbit anti-mouse IgG antibodies coupled to HRP were used as secondary antibody.

Figure 3:
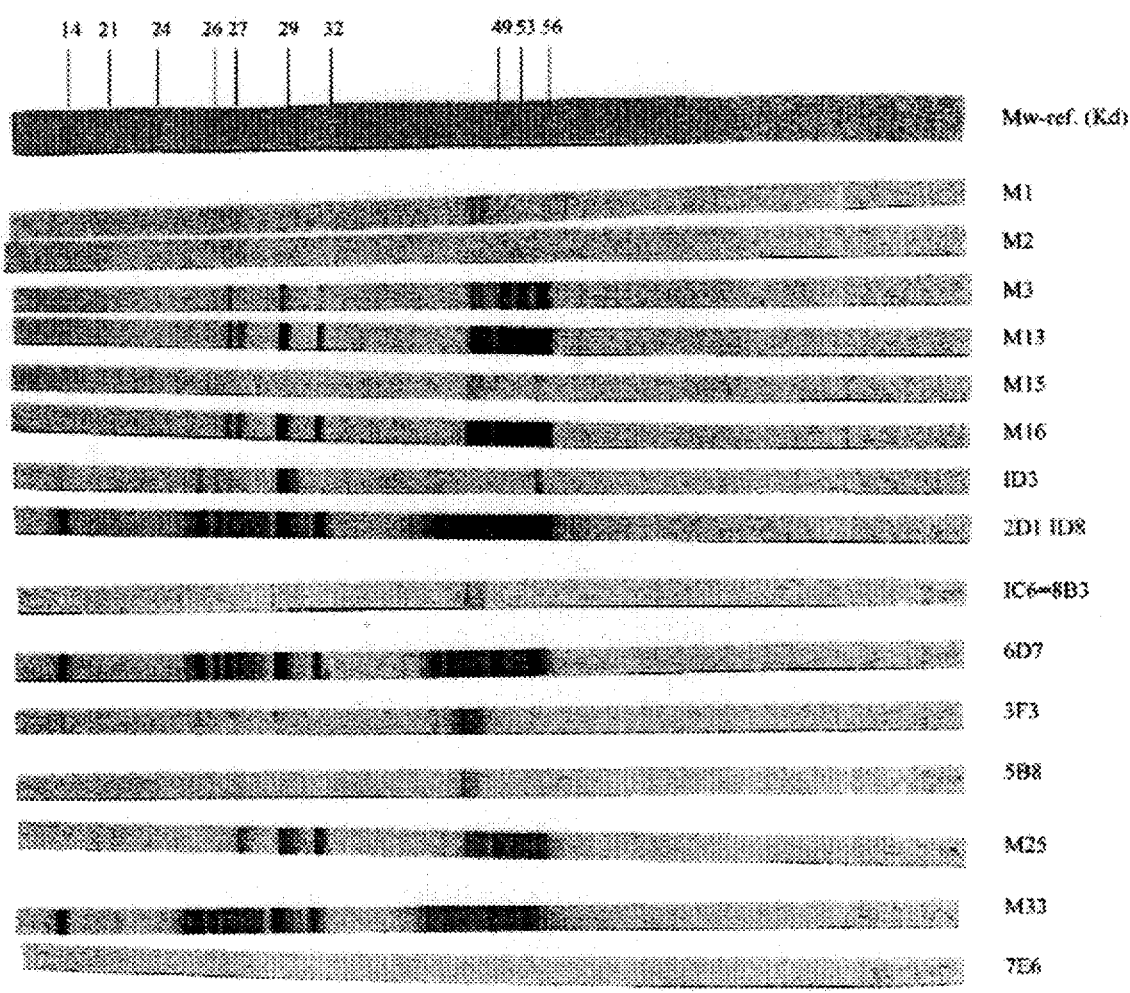
FIG. 3 shows a Western blot on a nitrocellulose filter after SDS-PAGE of purified cytokeratin 8 fragmented with chymotrypsin according to the present invention.

FIG. 3 shows a Western blot on a nitrocellulose filter after SDS-PAGE of purified cytokeratin 8 fragmented with chymotrypsin according to the invention. Each strip of nitrocellulose was allowed to react with different monoclonal antibodies produced as above. A secondary antibody, rabbit anti mouse IgG coupled with HRP, was added thereafter and the reaction of the monoclonals was visualized with a substrate DAB (Sigma D-5905) according to known method. The results show that several of the monoclonal antibodies react with several of the cytokeratin 8 fragments within the size range of about 10 to 50 Kd.

Figure 4:
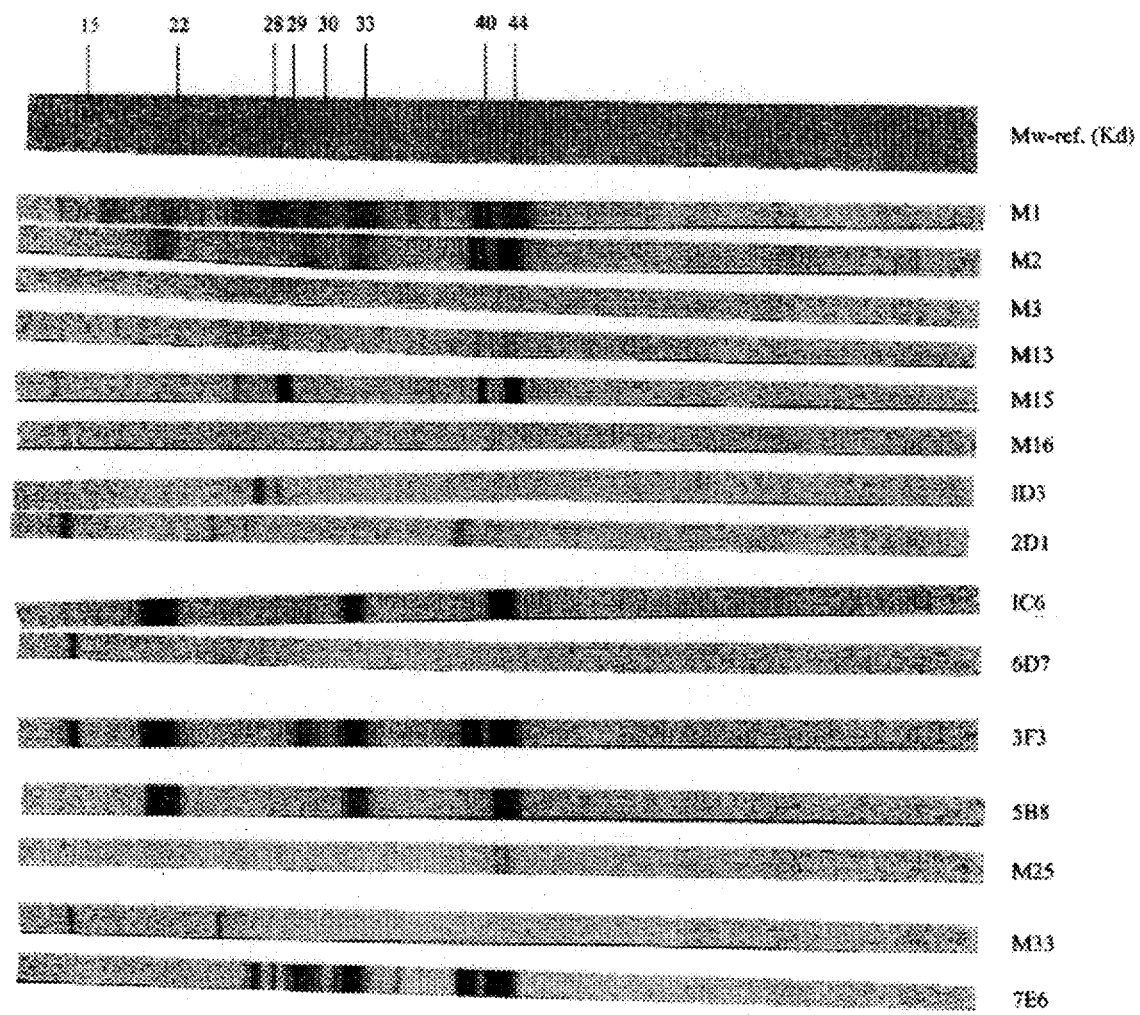
FIG. 4 shows a Western blot on nitrocellulose after SDS-PAGE of purified cytokeratin 18 fragmented with chymotrypsin.

In FIG. 4 there is shown a Western blot on nitrocellulose after SDS-PAGE of purified cytokeratin 18 fragmented with chymotrypsin. Each strip of nitrocellulose was allowed to react with different monoclonal antibodies produced as above. A secondary antibody, rabbit anti-mouse IgG coupled with HRP, was added thereafter and the reaction of the monoclonals was visualized with a substrate DAB (Sigma D-5905) according to a known method. The results show that several of the monoclonal antibodies react with several of the cytokeratin 18 fragments within the size range of about 10 to 44 Kd.

Figure 5:
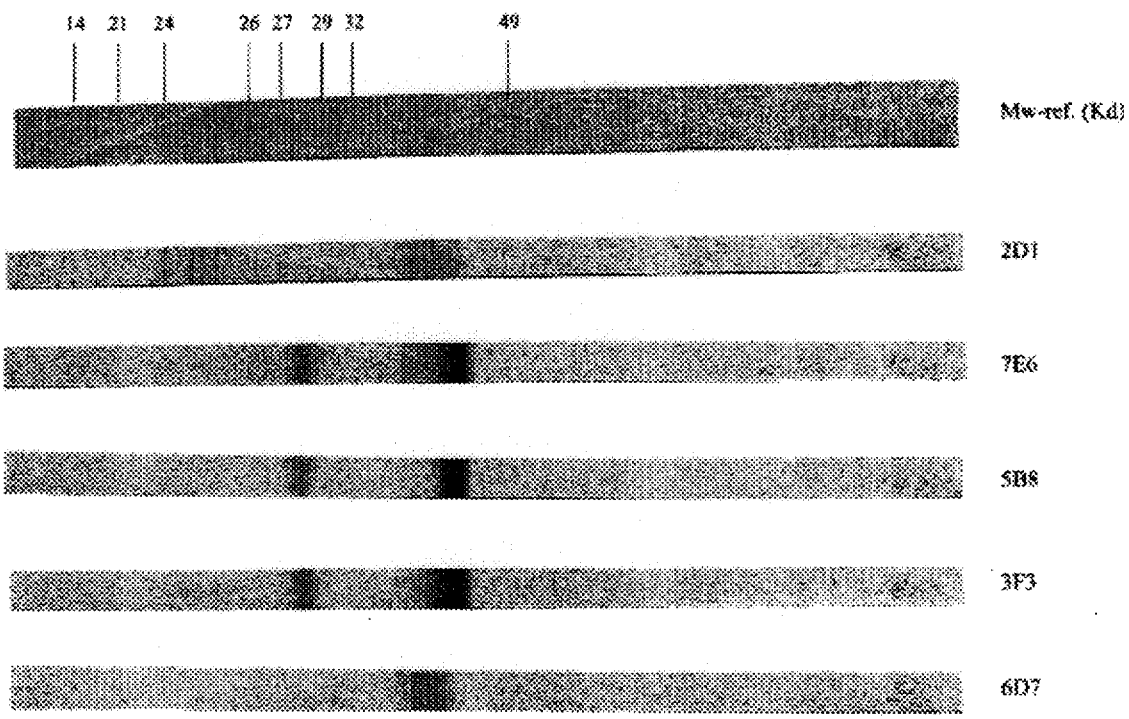
FIG. 5 shows a Western blot on nitrocellulose after SDS-PAGE of purified cytokeratin 19 fragmented with chymotrypsin.

In FIG. 5 there is shown a Western blot on nitrocellulose after SDS-PAGE of purified cytokeratin 19 fragmented with chymotrypsin. Each strip of nitrocellulose was allowed to react with different monoclonal antibodies produced as above. A secondary antibody, rabbit anti-mouse IgG coupled with HRP, was added thereafter and the reaction of the monoclonals was visualized with a substrate DAB (Sigma D-5905) according to a known method. The results show that several of the monoclonal antibodies react with several of the cytokeratin 19 fragments within the size range of about 10 to 38 Kd.

All together, the monoclonals show very good reactivity and specificity against a majority of fragments from cytokeratin 8 for 7 clones, from cytokeratin 18 for 7 clones, and from cytokeratin 19 for 5 clones. This is in agreement with the specificity of the 15 clones for the whole cytokeratins (see FIGS. 1–2).

Selection of the monoclonal antibodies is made based on the above tests as well as a test in which the antibodies do not react with other human proteins.

IN VITRO APPLICATIONS OF THE ANTIBODIES ACCORDING TO THE INVENTION

Test for Cytokeratin in Serum Samples from Cancer Patients and Healthy Persons

By IRMA and ELISA methods in which monoclonal antibody according to the present invention has been coupled to a solid phase (plastic tube) and polyclonal or monoclonal antibody has been labelled with Iodine-125 or HRP, sera from apparently healthy persons (blood donors) and sera from cancer patients were tested. As reference and standard material soluble cytokeratin fragments according to the invention in buffer solution and human serum was used. The levels from the different groups clearly showed different quantities (in ng/ml) of cytokeratin fragments.

Figure 6:
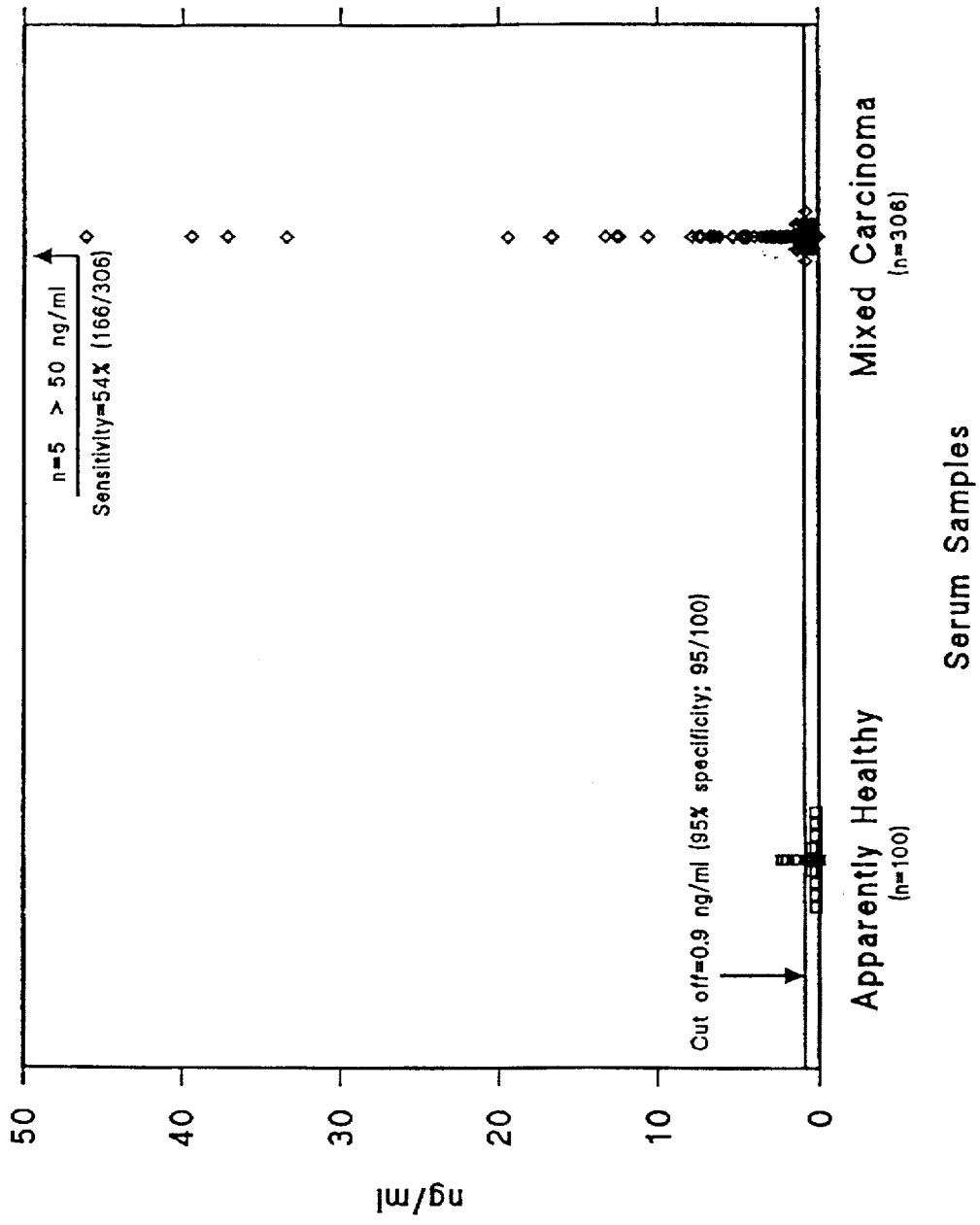
FIG. 6 shows, by ELISA, that the serum from apparently healthy persons gives a low response to monoclonal antibodies of the present invention, with a very low spread. The majority (95%) of the population falls under 0.9 ng/ml. For serum from the majority (54%) of cancer patients, the values are significantly higher.

The results in FIG. 6 show that serum from apparently healthy persons gives a low response in the test, with a very low spread. The majority (95%) of the population falls under 0.9 ng/ml. For serum from the majority (54%) of the cancer patients the values are significantly higher.

The above described shows that the present inventors have been able to detect cytokeratin fragments in serum, without any pretreatment thereof, distributed from tumours of cancer patients, using the antibodies and reagents that have been described in the present application. The antibodies according to the invention are able to react with the most representative fragments from the above cytokeratins in body fluids of man.

Figure 7:
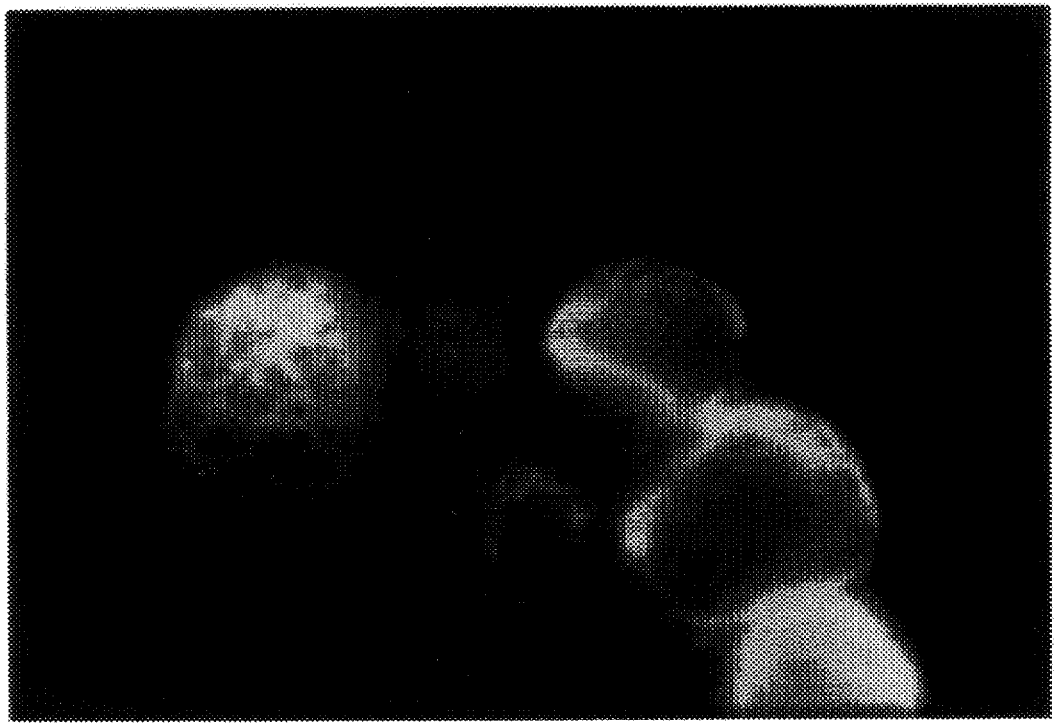
FIG. 7 shows cultivated tumour cells (MCF-7) which have been fixed with methanol (to open up the cell membrane) and thereafter incubated with one of the monoclonal antibodies (M1) according to the present invention, followed by a secondary antibody with FITC coupled thereto.

Furthermore, the antibodies according to the present invention are able to react with intact cell and tissue samples. FIG. 7 shows cultivated tumour cells (MCF-7) which have been fixed with methanol (to open up the cell membrane) and thereafter incubated with one of the monoclonal antibodies (M1) according to the present invention, followed by a secondary antibody with FITC coupled thereto. Illumination through a UV light microscope shows the typical cytoskeleton pattern within the cell for several of the cells.

Figure 8:
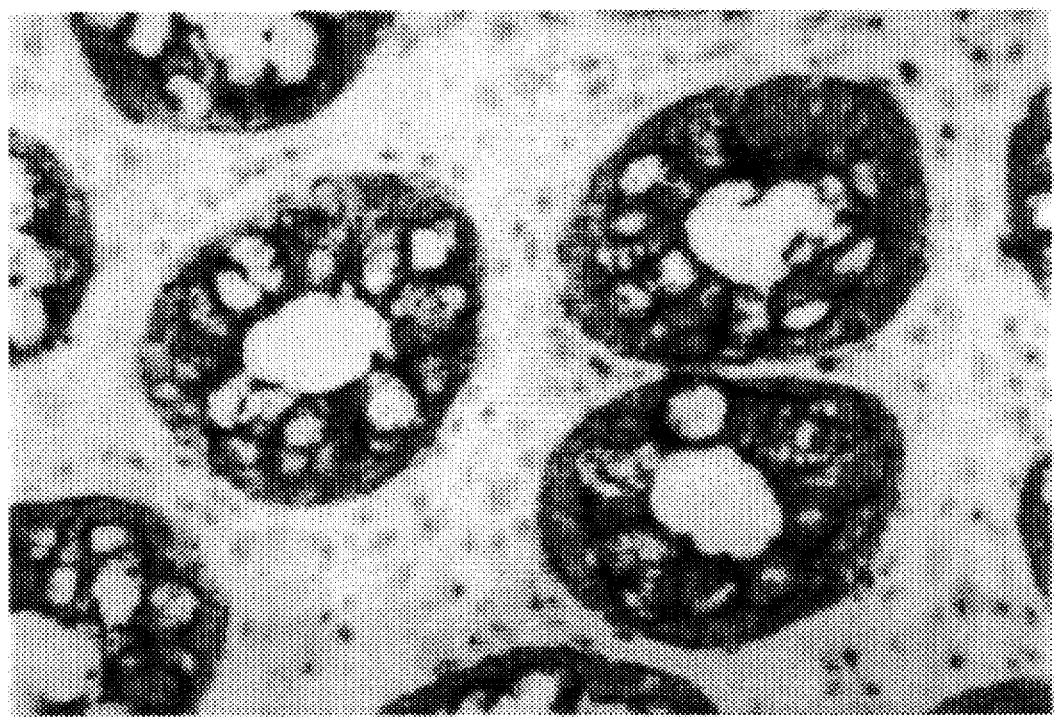
FIG. 8 shows an immunohistological section of an adenoma carcinoma of the colon.

Furthermore, the antibodies of the present invention enable immunohistology of tissue sections, and immunocytology of, for example, cervix smears, without elaborate pretreatment. FIG. 8 shows an immunohistological section of an adenoma carcinoma of the colon. This section is prepared by standard techniques and the cytokeratins in the sample appear by using peroxidase staining. Simple epithelia and tumour cells are revealed.

IN VIVO APPLICATIONS OF THE ANTIBODIES ACCORDING TO THE INVENTION

Figure 9:
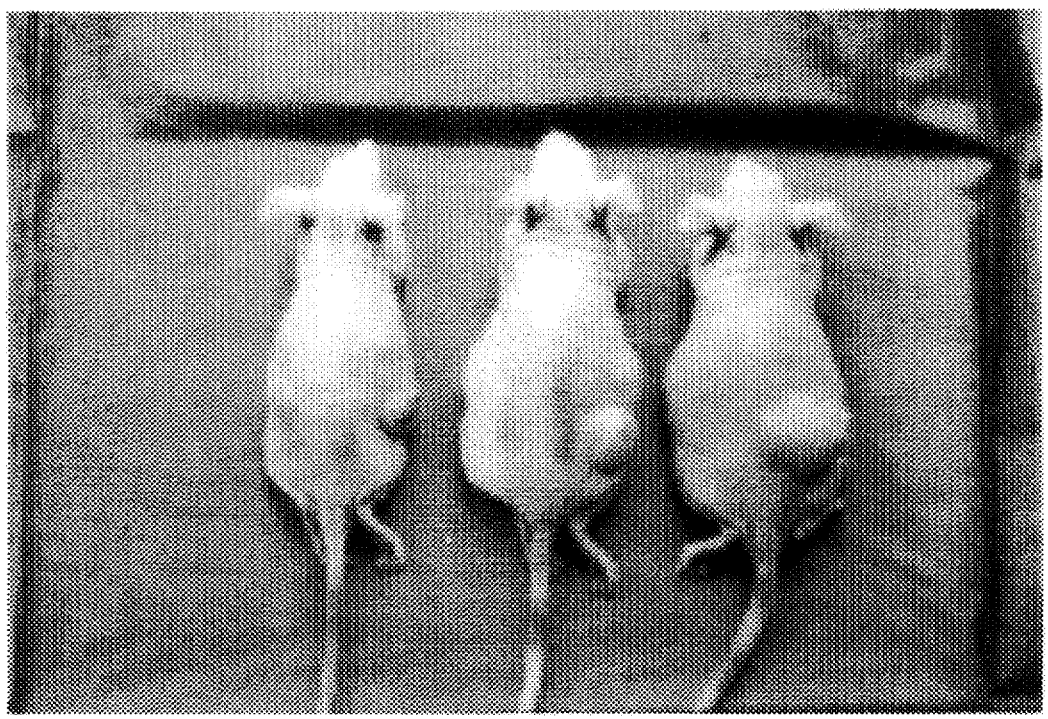
FIG. 9 shows mice inoculated with DU 145 cells and with developed tumours.

FIG. 9 shows mice inoculated with DU 145 cells and with developed tumours. The object of this experiment was to show that radioactively labelled monoclonal antibodies were able to localize implanted DU 145 tumours in mice. The cell line DU 145 has been shown to comprise cytokeratins 8 and 18. (Sherwood E. R., Berg L. A., Mitchell N. J.; The Journal of Urology, Vol 143, Jan. 1990, pp 167–171).

In blotting of SDS-PAGE, the tested monoclonal antibodies have been shown to react with the following cytokeratins and their fragments:

| MAb | CYK 8 | CYK 18 | Fragments 8 | Fragments 18 |
| --- | --- | --- | --- | --- |
| 6D7 | yes | yes (less) | yes | no |
| 2D1 | yes | yes (less) | yes | no |
| 3F3 | no | yes | yes (less) | yes |

12 mice of NMRI type with an average weight of about 25 g obtained from Bomhults farm, Denmark, were inoculated s.c. with 10 million DU 145 cells in RPMI 1640 including 10% FCS. The DU 145 cells were obtained from the research laboratory of the Akademiska hospital, Uppsala, Sweden.

The tumour cells were allowed to grow for 14 days and thereafter the mice were randomly divided in 4 groups of 3 mice each.

The monoclonal antibodies and normal mouse IgG (as a control) were labelled with $^{125}I$ by using Chloramine-T according to conventional procedures.

The respective group was provided with the following radioactively labelled antibodies in an amount of 0.3 ml/mouse:

| Group | Ab | Amount of Ab μg | Dosis μCi | Spec. Act. μCi/μg | Conc. μCi/ml |
|---|---|---|---|---|---|
| 1 | 6D7 | 2.5 | 12.6 | 5.0 | 42 |
| 2 | 2D1 | 2.7 | 22.5 | 8.5 | 75 |
| 3 | 3F3 | 0.71 | 4.3 | 6.0 | 14.2 |
| 4 | XXX | 2.8 | 14.4 | 5.1 | 48 |

XXX = Normal mouse IgG

Scintigraphy for about 20 minutes of choral hydrate anaesthtized mice was performed after 3, 5 and 9 days. After day 9, the mice were sacrified and weight and radioactivity of different organs was determined.

An evaluation of the scintigrammes gives the following results:

| Day | 6D7 | 2D1 | 3F3 | Normal mouse IgG |
|---|---|---|---|---|
| 3 | 3/3 ++ | 2/3 + | 2/3 ++ | – |
| 5 | 3/3 ++ | 2/3 + | 2/3 ++ | X |
| 9 | 3/3 +++ | 1/1 +++[1] | 3/3 +++ | – |

[1] = Two mice died of other reasons
X = not done
– = no localization of the tumour
+ = weak localization of the tumour
++ = localization of the tumour
+++ = marked localization of the tumour.

Figure 10:
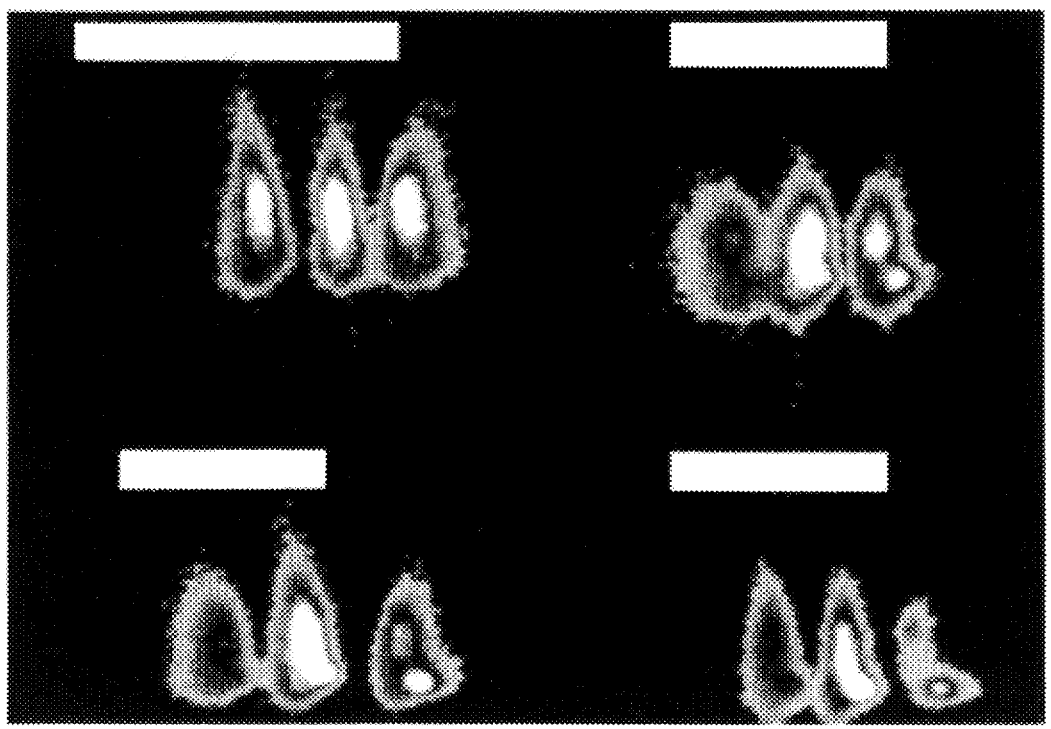
FIG. 10 shows scintigraphy of the mice of FIG. 9 showing the in vivo localizations of the tumours.

FIG. 10 shows scintigraphy of the mice of FIG. 9 showing the in vivo localizations of the tumours.

Figure 11:
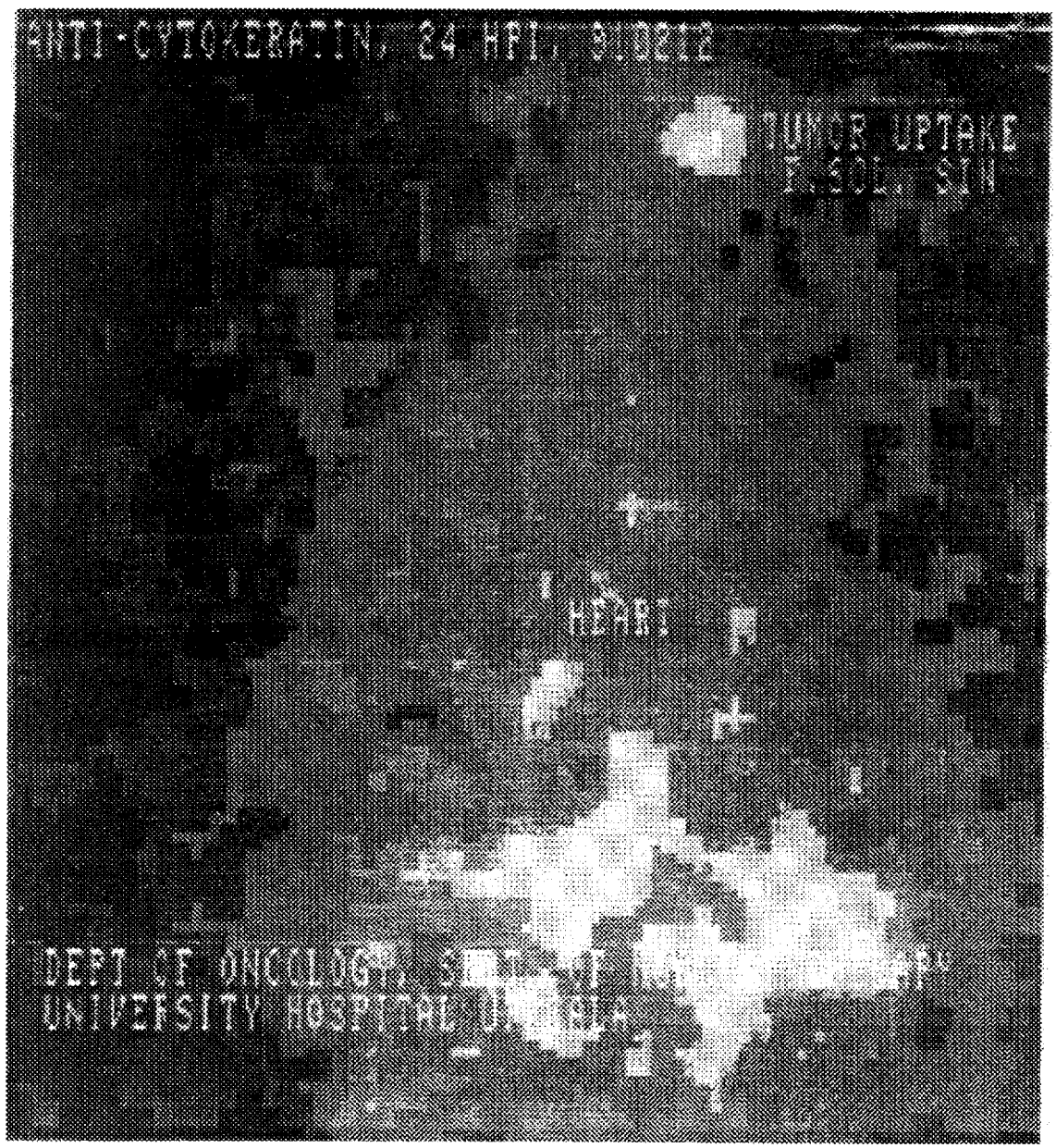
FIG. 11 shows an immunoscintigraphy image of a human being.

FIG. 11 shows an immunoscintigraphy image of a human being. The antibody 6D7 is purified and controlled to a quality corresponding to the demands of drugs. Thereafter it has been labelled with the radioactive isotope I 131. Following further purification it was injected into a patient having known tumour localizations. The patient was thereafter measured with equipment for measuring radioactivity, and the colour scale indicates the amount of radioactivity: light colour means much radioactivity and dark colour means no activity. 24 hours after the injection (24 HPI) there was significantly increased radioactivity on all known tumour localizations and from the image corresponding to the upper part of the chest it clearly appears that even a small metastase in the size range 1 cm can be detected with the radioactive labelled antibody 6D7. The large light portion of the image corresponds to the heart with its contents of blood. Still after 24 hours the blood contains some radioactive labelled antibody. Radioactive I 131 falls off the antibody and is secreted in the urine, and the antibody is degraded by the body to amino acids with time.

The monoclonal antibodies according to the present invention may also be used for in vivo cancer treatment by coupling to cytotoxins or radioactive isotopes, in order to kill tumour cells when the antibodies are localized in the tumour.

APPLICATION OF THE CYK FRAGMENTS ACCORDING TO THE INVENTION

The cytokeratin fragments according to the invention, besides the use for production of antibodies, can also be used:

for vaccination of tumour patients, per se or in combination with other treatment methods.

in kits to perform immunochemical tests, for example ELIZA, EIA, IRMA, LIA.

If the fragments are going to be used as a vaccine or antigen/reference material in immunological tests, the optional SDS PAGE described above is performed and the unwanted effects of SDS are avoided by diluting the fragment solution about 1000 fold in serum or, preferably (especially vaccine) in albumin solutions. The addition of proteins also avoids aggregation of the fragments and provides a "dispersing" effect on the epitopes, with inert proteins. The purification and use of the fragments as a vaccine will have to follow the special purity demands of the registration process in the respective country.

In "sandwich assays" or "double site assays" the cytokeratin fragments are used as standard and reference material and the antibodies are either used as catching antibody coupled to solid phase, i.e., microtiter plates, or as tracer antibody labelled in a suitable way to detect the analyte, i.e., cytokeratin fragment. In "single site assays" the cytokeratin fragments are coupled to a solid phase and an anti antibody is used to detect the target substance, i.e., the human antibody against the cytokeratin fragment.

Figure 12:
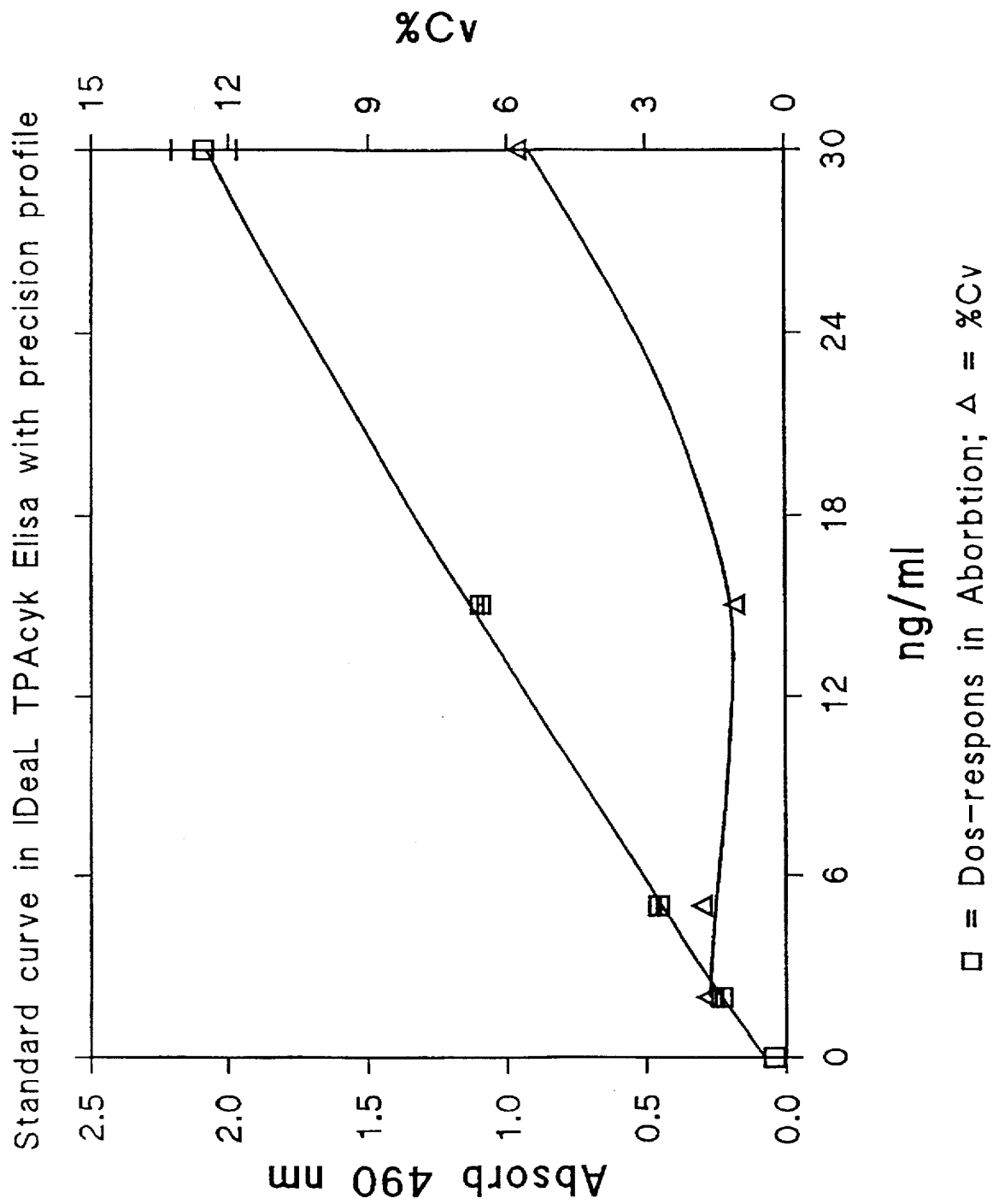
FIG. 12 shows the sensitivity of immunological tests performed with fragments according to the present invention. This figure shows a dose-response curve and the precision profile of an ELISA test using fragments according to the present invention as standard/reference material and the monoclonals coated to microtiter plates. The sensitivity calculated as average value +2 SD is as low as 0.1 ng/ml, which proves to be a very high sensitivity.
Figure 13:
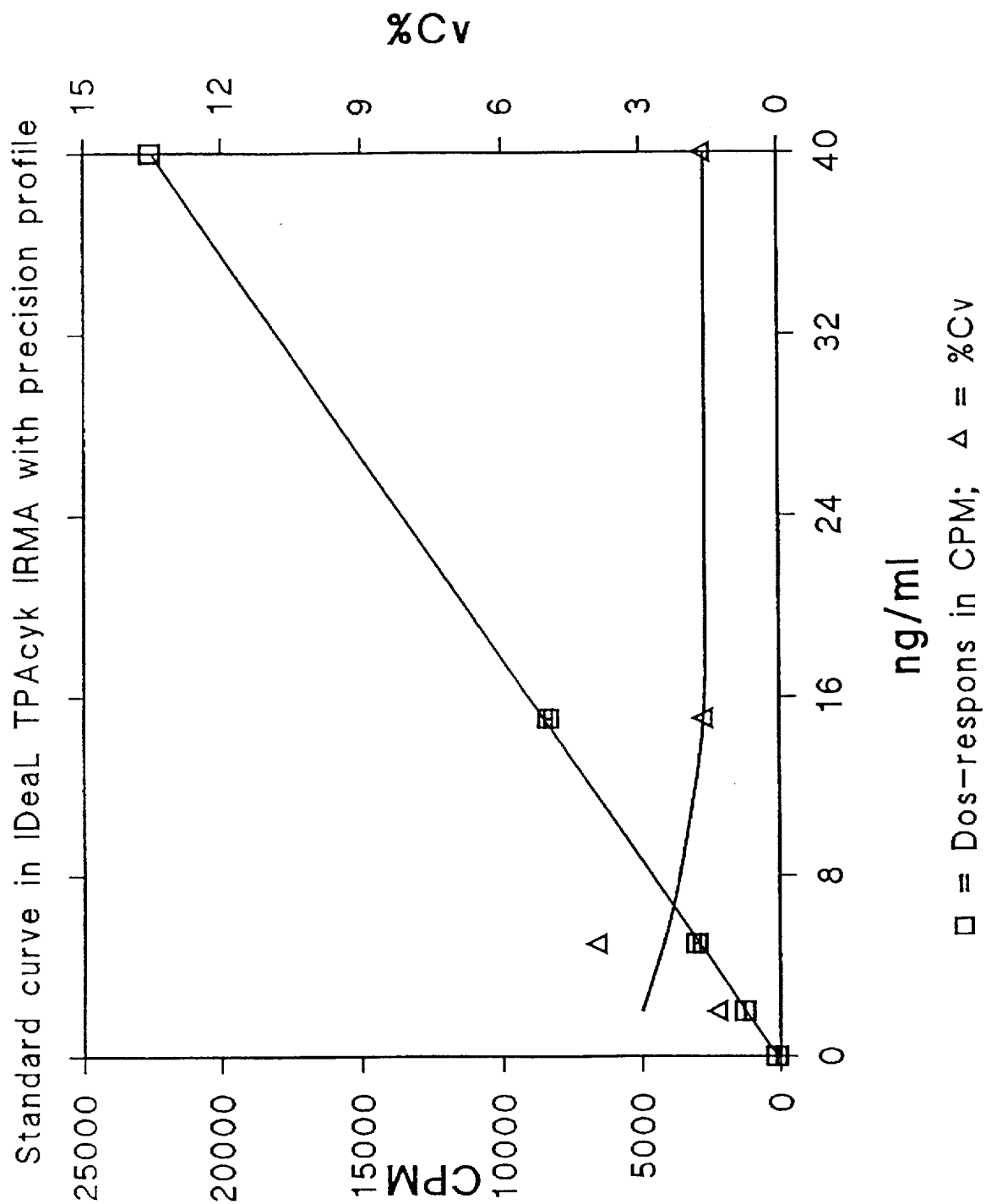
FIG. 13 shows the sensitivity of immunological tests performed with the fragments according to the present invention. Results similar to those shown in FIG. 12 are obtained in an IRMA test.

The sensitivity of the immunological tests performed with the fragments according to the invention is shown in FIGS. 12 and 13.

FIG. 12 shows a dose-response curve and the precision profile of an ELISA test using the fragments according to the invention as standard/reference material and the monoclonals coated to the microtiter plates. The sensitivity (calculated as average value +2 SD) is as low as 0.1 ng/ml, Which proves to be a very high sensitivity.

The same excellent results are obtained in an IRMA test which is shown in FIG. 13.

These sensitive tests are expected to have great applicability in checking the growth rate in body fluids (without pretreatment) from epithelial cancer patients and evaluating the effects of monoclonal antibody therapy.

Abbreviations

ATCC: American Type Culture Collection
cpm: counts per minute
CYK or CK: cytokeratin
DAB: 3,3'-Diaminobenzidine-tetra-hydrocloride
FIA: Freund's incomplete adjuvans
FCA: Freund's complete adjuvans
FCS: fetal calf serum
IRMA: Immunoradiometric assay
ELISA: Enzyme linked immunosorbent assay
LIA: Luminiscence immunoassay
Kd: Kilodalton
HRP: Horse redish peroxidase
FITC: Fluorescein isothiocyanate
PBS-EDTA: Phosphate buffered saline-ethylende diamine tetra acetic acid
RIA: Radio immunoassay
RT: Room Temperature
SDS-PAGE: Sodium dodecyl sulphate-poly acrylamide gel electrophoresis

We claim:

1. An immunochemical testkit to detect cancer of epithelial origin in body fluids, comprising:
 a mixture of cytokeratin fragments; and
 monoclonal antibodies which bind to said cytokeratin fragments;

wherein said mixture of cytokeratin fragments is produced by the method of:

purifying cytokeratins from epithelial carcinoma cells by preparative SDS-PAGE;

eluting bands corresponding to cytokeratins 8, 18, and 19;

digesting said cytokeratins 8, 18, and 19 to produce a mixture of fragments ranging in size from 10 to 50 kD, with the proviso that said mixture includes fragments other than fragments ranging in size from about 38 to 40 kD; and wherein said monoclonal antibodies which bind to said cytokeratin fragments are produced by the method of:

immunizing a mouse with a solution comprising said mixture of cytokeratin fragments;

recovering lymphocytes from the spleen of said mouse;

fusing said lymphocytes with myeloma cells to produce hybridomas;

cloning and growing said hybridomas;

stabilizing and establishing single clones of said hybridomas; and recovering a monoclonal antibodies which bind to said cytokeratin fragments from said single clones of said hybridomas.

2. The immunochemical testkit of claim 1, wherein said digesting said cytokeratins 8, 18, and 19 is performed by a method selected from the group consisting of enzymatic cleavage wherein the enzyme is selected from the group consisting of chymotrypsin, V8 protease, and pepsin; chemical cleavage wherein the chemical is selected from the group consisting of cyanogen bromide and 3-bromo-3-methyl-2-(2-nitrophenylmercapto)-3H-indole; and partial hydrolysis.

3. The immunochemical testkit of claim 1, wherein said digesting said cytokeratins 8, 18, and 19 is performed enzymatically using chymotrypsin.

4. A method of producing antibodies against cytokeratin fragments, comprising:

purifying cytokeratins from epithelial carcinoma cells by preparative SDS-PAGE;

eluting bands corresponding to cytokeratins 8, 18, and 19;

digesting said cytokeratins 8, 18, and 19 to produce a mixture of fragments ranging in size from 10 to 50 kD, with the proviso that said mixture includes fragments other than fragments ranging in size from about 38 to 40 kD;

immunizing an animal with a solution comprising said mixture of cytokeratin fragments; and recovering antibodies which bind to said cytokeratin fragments from said animal.

5. The method of claim 4, wherein said digesting said cytokeratins 8, 18, and 19 is performed by a method selected from the group consisting of enzymatic cleavage wherein the enzyme is selected from the group consisting of chymotrypsin, V8 protease, and pepsin; chemical cleavage wherein the chemical is selected from the group consisting of cyanogen bromide and 3-bromo-3-methyl-2-(2-nitrophenylmercapto)-3H-indole; and partial hydrolysis.

6. The method of claim 4, wherein said digesting said cytokeratins 8, 18, and 19 is performed enzymatically using chymotrypsin.

7. The method of claim 6, wherein said digesting said cytokeratins 8, 18, and 19 with chymotrypsin is performed using a weight ratio of chymotrypsin:cytokeratin of about 1:50 to 1:1000, wherein the activity of said chymotrypsin is 40 to 60 units per mg of protein, the concentration of cytokeratin is 0.2 mg/ml, and said digesting is carried out at a temperature of 37° C.

8. The method of claim 6, wherein said digesting said cytokeratin with chymotrypsin is performed using a weight ratio of chymotrypsin:cytokeratin 8 of 1:400, a weight ratio of chymotrypsin:cytokeratin 18 of 1:100, and a weight ratio of chymotrypsin:cytokeratin 19 of 1:75.

9. A method of producing a monoclonal antibody against cytokeratin fragments, comprising:

purifying cytokeratins from epithelial carcinoma cells by preparative SDS-PAGE;

eluting bands corresponding to cytokeratins 8, 18, and 19;

digesting said cytokeratins 8, 18, and 19 to produce a mixture of fragments ranging in size from 10 to 50 kD, with the proviso that said mixture includes fragments other than fragments ranging in size from about 38 to 40 kD;

immunizing a mouse with a solution comprising said mixture of cytokeratin fragments;

recovering lymphocytes from the spleen of said mouse;

fusing said lymphocytes with myeloma cells to produce hybridomas;

cloning and growing said hybridomas;

stabilizing and establishing single clones of said hybridomas; and recovering a monoclonal antibody which binds to said cytokeratin fragments from said single clones of said hybridomas.

10. The method of claim 9, wherein said digesting said cytokeratins 8, 18, and 19 is performed by a method selected from the group consisting of enzymatic cleavage wherein the enzyme is selected from the group consisting of chymotrypsin, V8 protease, and pepsin; chemical cleavage wherein the chemical is selected from the group consisting of cyanogen bromide and 3-bromo-3-methyl-2-(2-nitrophenylmercapto)-3H-indole; and partial hydrolysis.

11. The method of claim 9, wherein said digesting said cytokeratins 8, 18, and 19 is performed enzymatically using chymotrypsin.

* * * * *